United States Patent [19]
Brown

[11] 3,967,627
[45] July 6, 1976

[54] HOT/COLD APPLICATOR SYSTEM
[75] Inventor: Billy E. Brown, Indianapolis, Ind.
[73] Assignee: Moore-Perk Corporation, Indianapolis, Ind.
[22] Filed: Nov. 18, 1974
[21] Appl. No.: 524,572

[52] U.S. Cl. .............................................. 128/400
[51] Int. Cl.[2] ........................................... A61F 7/00
[58] Field of Search ........... 128/399, 400, 402, 254, 128/258, 378, 379, 303.1; 62/3

[56] References Cited
UNITED STATES PATENTS

| 484,182 | 10/1892 | Dewey | 62/3 |
|---|---|---|---|
| 3,074,410 | 1/1963 | Foster | 128/400 |
| 3,088,288 | 5/1963 | Elfring | 62/3 |
| 3,262,492 | 7/1966 | Meenan | 62/3 X |
| 3,738,372 | 6/1973 | Shioshrili | 128/400 |

Primary Examiner—Lawrence W. Trapp
Attorney, Agent, or Firm—Dawson, Tilton, Fallon & Lungmus

[57] ABSTRACT

Heat transferring liquid is pumped by a peristaltic pump from a reservoir through a heat exchanger to a disposable applicator pad through flexible conduits. The heat exchanger is provided with thermoelectric diodes which, under control of electronic circuitry, may absorb heat from or transfer heat to the liquid. Further, the control circuitry permits adjustment of the temperature of the applicator pad, whether hot or cold.

13 Claims, 4 Drawing Figures

HOT/COLD APPLICATOR SYSTEM

BACKGROUND AND SUMMARY

The present invention relates to a system for selectively applying either heat or cold to a local area, and particularly when it is desired that the temperature of the applicator be held substantially constant. The present invention is useful in many areas, principally in the medical field. One of the advantages of the present system is that, depending upon the applicator pad which is attached to the system, the applicator may be used as a conventional external applicator, or it may be used during surgery to apply to incisions or open wounds, or it may be used to rapidly cool or re-heat an organ during transplant, etc.

The present invention is preferably used with an applicator pad of the type disclosed in co-owned U.S. patent application Ser. No. 381,733, of Francis C. Moore and Leon R. Perkinson, for "Disposable, Sterile Temperature Control Applicator Pad for Medical Application", filed July 23, 1973.

Heat applicators have long been used in the medical field, and they frequently take the form of a padded or blanket type of applicator provided with internal resistive wiring for generating heat. Probably the most commonly used type of cold applicator in the medical field is a flexible plastic package containing two chemicals which, when mixed absorb heat. The chemicals are packaged on either side of a rupturable membrane so that the application of pressure to the exterior of the package ruptures the membrane and causes the fluids to mix and producing the heat-absorbing reaction. Another type of cold applicator uses a compressor, refrigerant, condensing and evaporator coils, and a permanent or non-disposable applicator. Such units are heavy and cumbersome.

The present invention uses a heat transferring liquid stored in a reservoir, such as a standpipe, which is pumped by a peristaltic pump through a heat exchanger containing thermoelectric diodes. As is known, if a current is forced in one direction (anode to cathode) through a thermoelectric diode, the diode will produce heat through ohmic losses. If a voltage of opposite polarity is applied to the junctions of the diode, then the diode will absorb heat from its surrounding area. Control circuitry, under control of an operator, determines which polarity of electrical potential is applied to the thermoelectric diodes in the heat exchanger, and in either case the applied voltage is a rectified sine wave. The control circuitry also determines the firing angle at which the applied voltage is coupled to the thermoelectric diodes, and this firing angle is adjustable. Hence, the operator, in addition to determining whether the system will supply heat to the transfer liquid or absorb heat from the transfer liquid, may adjust the temperature of the transfer liquid in either the hot or cold region. A temperature-sensitive transducer is associated with the passageway from the transfer liquid reservoir and included in the electronic control circuitry in such a way as to regulate the temperature of the transfer liquid once a setting has been made by the operator.

Another feature of the invention is that a second subsystem of reservoir, heat exchanger and pump may be used, connecting the shaft of the second peristaltic pump in tandem with the shaft of the first so that they are driven by a single motor. In this system, the second fluid system may be used, for example, to flush a transplant organ with saline solution at a controlled temperature, either hot or cold or successively cold and hot. Thus, great flexibility in usage is provided. In the case of one heat transferring liquid system, it is preferred that the total liquid in the system, including reservoir, heat exchanger and tubing be less than about two quarts, and the liquid may be water. This permits a very rapid response in the applicator pad to changes in temperature setting. Further, the present system provides greater conduction of heat to or from the application surface because it permits the use of a wet applicator pad. Such pad, as disclosed in the above-identified application further permits the application of medicaments or sterilizing agents to the application area.

Other features and advantages of the present will be apparent to persons skilled in the art from the following detailed description of a preferred embodiment accompanied by the attached drawing.

THE DRAWING

DETAILED DESCRIPTION

Figure 1:
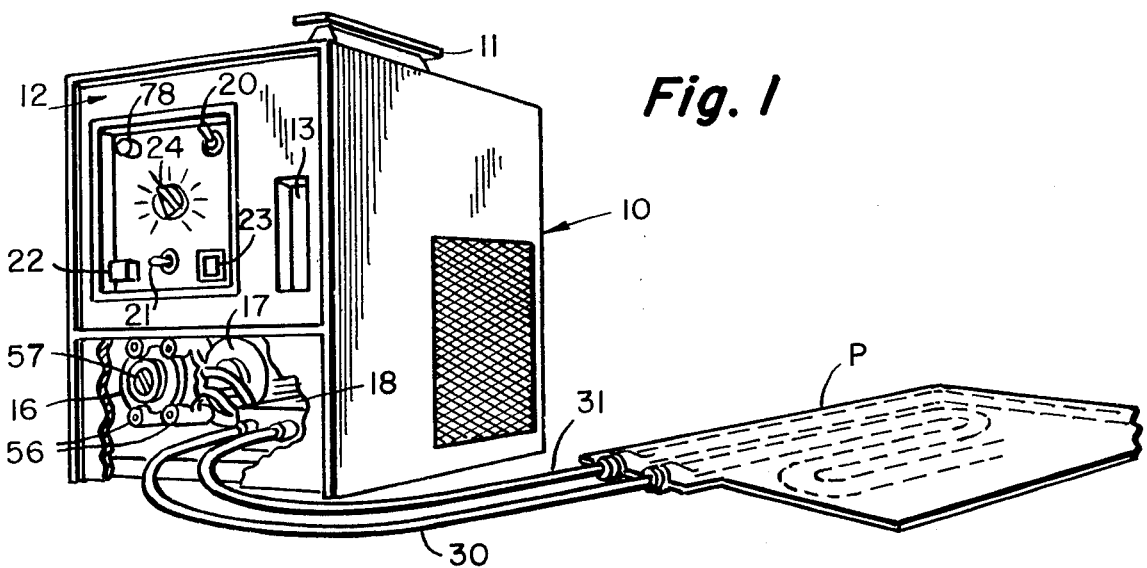
FIG. 1 is a perspective view, partly broken away, of a system constructed according to the present invention.

Referring then to FIG. 1, reference numeral 10 generally designates a console which houses the heat exchanger, pump, control circuitry and so on for the present invention. The console 10 is portable, including an upper handle 11. The front portion of the console 10 includes a faceplate panel 12 on which are mounted the operator controls and signal lights. A window 13 in the faceplate panel 12 permits the operator to view the amount of heat transferring liquid which is present in the reservoir. Preferably, the rerservoir takes the form of a standpipe, designated 14 in FIG. 2, the heat-transferring liquid being denoted 15.

Returning to FIG. 1, a peristaltic pump 16 is mounted to the lower portion of the faceplate panel 12, and the lower portion of that panel is partially broken away to show a drive motor 17 and a fluid manifold 18, to be discussed presently.

On the faceplate panel 12, there are an ON/OFF switch 20, a hot/cold switch 21, a green indicator light 22 for "COLD" a red indicator lamp 23 for "HOT", and a manually adjustable temperature dialing switch 24.

The heat-transferring liquid is communicated from the applicator 18 through a first conduit 30 to an applicator pad generally designated P; and the liquid is returned to the manifold 18 by means of a second conduit 31. As indicated above, the pad P may be constructed according to the teachings of the above-identified patent application Ser. No. 381,733 of Francis C. Moore and Leon R. Perkinson, for "Disposable, Sterile Temperature Control Applicator Pad for Medical Application", filed July 23, 1973. Alternative shapes may be used, depending upon application; and briefly, the pad P includes two sheets of thin plastic material laminated together to form a serpentine conduit through which the heat transferring liquid is communicated, and an outer layer of absorbent material which may be wet in order to improve heat transfer qualities. Further, the pad P may be an applicator which has a special shape, depending upon the application area.

It is considered an important feature of the invention that the applicator pad P is disposable and may take on various forms as this greatly expands the utility of the system. By using a variable volume reservoir, such as a standpipe 14 for the heat-transferring liquid, the amount of liquid in the applicator pad P does not affect system operation. Further, by placement of the temperature-sensitive device as will be disclosed below, regulation of the temperature of the heat-transferring liquid is practically independent of load so that the design and volume of the applicator pad P does not seriously affect system operation.

Figure 2:
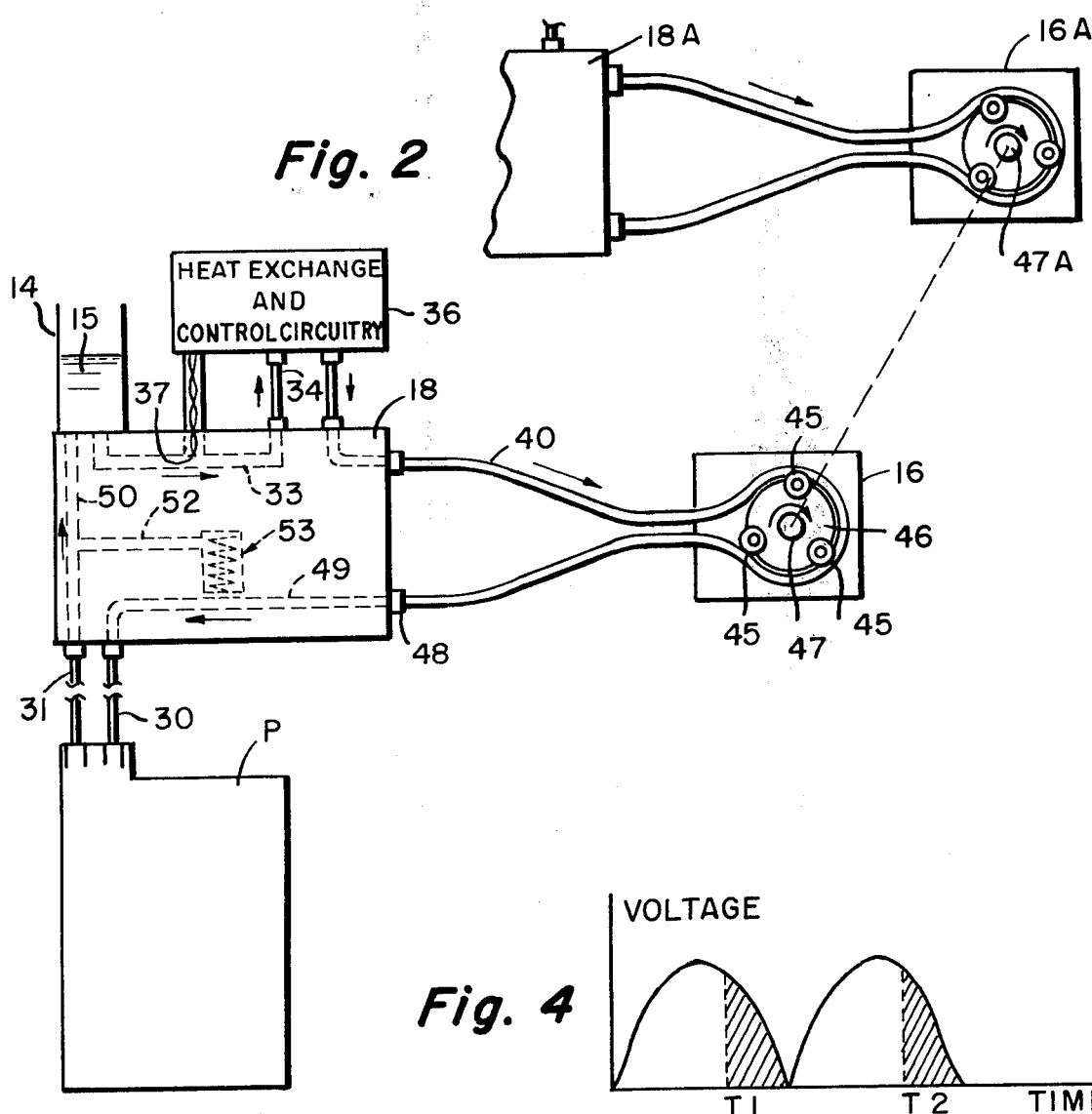
FIG. 2 is a diagrammatic showing of the elements of the heat transferring liquid loop, showing two pumps in tandem.

Turning now to FIG. 2, fluid 15 from the reservoir 14 is coupled through a bored conduit 33 and an exterior conduit 34 to the heat exchanger and control circuitry functionally indicated by the block 36. As mentioned, the height of the heat-transferring liquid 15 in the standpipe 14 may be observed through the window 13 on the faceplate panel of the console 10.

A temperature-sensitive resistor or "thermistor" 37 is located in the conduit 33 at a location adjacent the outlet of the reservoir 14 and, more importantly, sensing the temperature of the heat-transferring liquid prior to forcing the liquid through the heat exchanger or through the applicator pad (which represents the "load"). With this arrangement, control of the temperature of the heat-transferring liquid has been facilitated and made substantially independent of variations in load (within design range) such as may be caused by differences in contact area, differences in applicator pad heat-transfer characteristics or volume, and so on. The resistance of thermistor 37 is an inverse function of temperature. The control circuitry will be explained in more detail below.

After exiting from the heat exchanger, the heat transferring liquid flows back through the manifold 18 and a flexible tube 40 which forms a part of the peristaltic pump 16. Pumps of this type are well known in the medical field, comprising a plurality of freely rotatable orbital rollers 45 mounted between end plates, one of which is shown at 46. The end plates are driven in rotation by a shaft 47. A continuous fluid-tight tube, such as that shown at 40, is arranged in a race through the pump which is spaced from the outer ends of the rollers 45 a distance sufficient only to permit collapse of the tube 40, so that the shaft 47 turns, the orbital rollers 45 are moved to first close the flexible tube 40, then force a quantum of liquid trapped in it along the direction of movement of the orbital rollers to an outlet which, in this case, is coupled back to the manifold 18 at 48. The heat-transferring liquid is thence communicated through an internal bore 49 to the flexible conduit 30 and the applicator pad P. The liquid returning from the pad P through the conduit 31 is coupled to the standpipe 14 by means of a bore 50 which, again, is in the manifold 18. A conduit 52 communicates the fluid in the discharge bore 50 with a pressure relief valve 53 in the manifold 18. The input to the pressure relief valve 53 is coupled to the conduit 49 which feeds the applicator pad P. Thus, should the pad P or the flexible tubes 30, 31 become occluded, the resulting increase in pressure appearing in the conduit 49 will actuate the pressure relief valve 53, and the fluid will be transmitted directly to the reservoir or standpipe 14. This will prevent bursting of any portions of the system near the subject on whom the pad P is applied until the obstruction is removed or obviated.

As has already been mentioned, if it is desired to adapt the invention to include a second heating or cooling system which is controlled independently of the first, a second paristaltic pump 16A may be added, with its shaft 47A connected in tandem with the previously-mentioned shaft 47 of the pump 16, so that they are driven by a common motor. As best seen in FIG. 1, the housing for the pump 16 includes a number of bosses 56 which facilitate mounting of the second pump to the front of the console 10, and the shaft 47 may be slotted as at 57 to facilitate driving of the second shaft.

Referring again to FIG. 2, associated with the second pump 16A is a second manifold 18A as well as a second heat exchanger and control circuitry, reservoir, and so on, which are not shown because they may be similar to those corresponding elements which have already been disclosed. Thus, the second fluid system may contain a separate fluid and a separate control. This would be useful, for example, in a transplant operation wherein one applicator pad may be used to reduce edema on the incision or to surround the organ being transplanted, while the second fluid system could be used to flush the organ with a saline solution to preserve it.

Among the advantages of using a peristaltic pump are that electrical isolation between the applicator and the control system are greatly reduced, thereby reducing the shock hazard. Further, the fluid is completely isolated from the pumping mechanism and can therefore be maintained is a sterile condition if this is desired.

ELECTRICAL CONTROL SYSTEM

Figure 3:
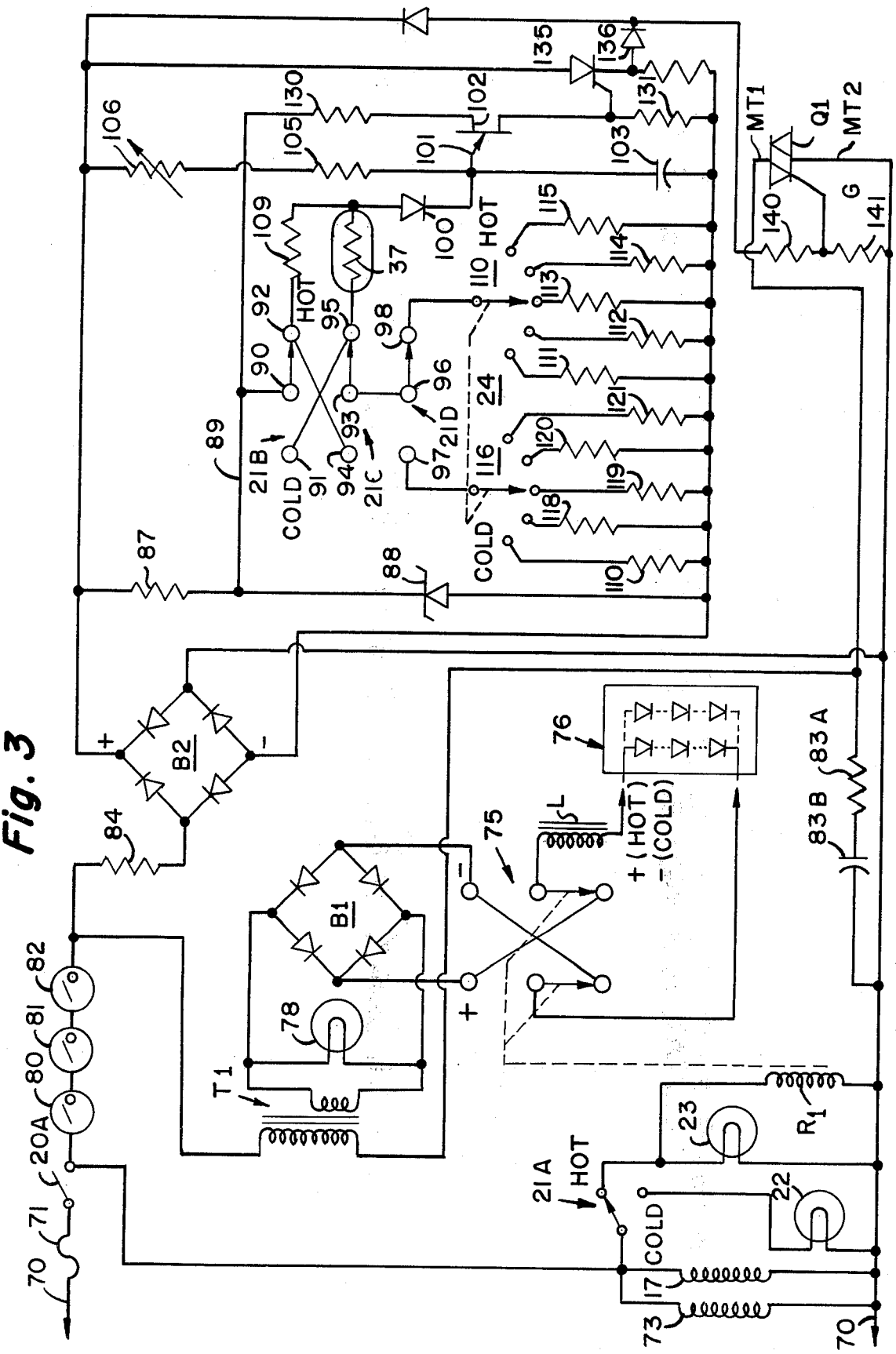
FIG. 3 is a circuit schematic diagram of the controller for the present invention.

Turning now to FIG. 3, reference numeral 70 designates the input lines from a conventional 120-volt, 60 Hz. source, such as wall outlet. One of the electrical feed lines is provided with a fuse 71 and the contacts 20A of the ON/OFF switch are also connected in this line. Preferably, the ungrounded or "HOT" line is fused and provided with the ON/OFF switch. Power is fed once the contacts 20A are closed to a fan motor 73 for circulating room air around the heat exchanger and to the winding of the motor 17 which drives the pump 16.

Power is also supplied to the HOT/COLD switch 21 which is a four-pole, double-throw switch having a "HOT" and a "COLD" position. One of the legs or decks of the switch 21, designated 21A in FIG. 3 is used to couple power to the filaments of the lamps 22, 23. In the position shown (namely, the "HOT" position), the red lamp 23 is illuminated, and power is also coupled to the coil of a relay $R_1$. The other four decks of the switch 21 are designated respectively 21B, 21C and 21D, and will be discussed below.

The contacts of the relay $R_1$ form a double-pole, double-throw switch generally designated 75 in the left half portion of FIG. 3. When the coil of the relay $R_1$ is energized, the contacts 75 are in the position shown for coupling energy through an inductor L to the thermoelectric diode bank generally designated by reference numeral 76.

Power is coupled to the contacts 75 from a bridge circuit B1 which, in turn, is energized by means of a transformer T1. An indicator lamp 78 is connected across the terminals of the secondary of the transformer T1, and this lamp is located on the faceplate panel to indicate to the operator that current is being fed to the thermoelectric diode bank 76, when it is lit. A series of three thermostats designated respectively 80, 81 and 82 are located between the main power switch 20A and the primary of the transformer T1. Each of the thermostats 80–82 is a normally-closed thermostatic switch such that if the ambient temperature exceeds a predetermined value, the switch opens. The thermostat 80 is located in the main power supply and will open if the temperature rises above 190° F. The thermostats 81 and 82 are both located in the heat exchanger, one opening at 130° F. and the other opening at 190° F., thereby providing a redundant protection against overheating in the heat exchanger.

The primary winding of the transformer T1, as mentioned, has one terminal connected to the "HOT" power line through the thermostats. The other terminal is coupled to the other power line through a controlled semi-conductor switch which, in the illustrated embodiment is a triac Q1. A resistor 83A and a capacitor 83B form a noise suppressing network connected between the second terminal of the primary winding of transformer T1 and ground or common. Thus, the polarity of voltage fed to the diode bank 76 is controlled by the contacts 75 of relay R1 which, in turn, is controlled by the manual selection switch 21A. However, the duty cycle or duration of coupling of power to the contact 75 from the bridge B1 is determined by control of the triac Q1, as will presently be discussed. Turning now to the upper left-hand portion of FIG. 3, a limiting resistor 84 couples power to a second bridge circuit B2. The output of the bridge B2 is coupled through a limiting resistor 87 to a Zener diode 88 which establishes a fixed DC potential for the subsequent circuitry, which potential is established on a line designated 89. The deck 21B of the switch 21 has a terminal 90 connected to the wiper blade and first and second fixed terminals 91, 92. Similarly, the deck 21C has a terminal 93 connected to the wiper arm and first and second fixed terminals 94 and 95. The deck 21D also has a terminal 96 connected to the wiper arm and first and second fixed terminals 97 and 98. The contact 91 of deck 21B is connected to the contact 95 of deck 21C. Similarly, contact 92 of deck 21B is connected to contact 94 of deck 21C. Terminals 93 and 96 respectively of decks 21C and 21D are also connected together.

It will be observed from the above that the decks 21B and 21C are connected to form a double-pole, double-throw switch. The thermistor 37, shown schematically in FIG. 3 as a resistive element is connected between the terminal 95 and the anode of a diode 100. The cathode of the diode 100 is connected to the gate lead 101 of a unijunction transistor 102. A capacitor 103 is connected between the gate lead 101 and the negative terminal of bridge B2. A fixed resistor 105 and a variable resistor 106 are connected in series between a positive terminal of the bridge B2 and the gate lead 101 of the unijunction 102. The junction between the thermistor 37 and diode 100 is coupled by means of a fixed resistor 109 to the contact 92 of the deck 21B.

The fixed contact 98 of the deck 21D is connected to the movable contact of a multi-position switch generally designated by reference numeral 110 and having five fixed contacts, as illustrated. Resistors 111–115 are connected respectively between these fixed contacts and the negative terminal of the bridge B2. Similarly, the fixed contact 97 of deck 21D is connected to the movable contact of a second multi-position switch generally designated 116. Fixed resistors 117–21 are connected respectively between these fixed contacts and the negative terminal of the bridge circuit B2.

The switches 110, 116 may be a decade switch having two separate decks, each deck being provided with ten individual contacts. However, only five contacts are used for each deck in a manner such that only one deck is connected to a resistor at a given time. That is, the switch 116 may have the first five positions connected to the resistors 117–21 whereas the switch 110 may have the second five positions connected to the resistors 111–115. The switches 110, 116 comprise the manually temperature control switch 24 of FIG. 1. The switch 116 controls the temperature when the system is operating in the "COLD" mode, and the switch 110 controls the temperature setting when the system is operating in the "HOT" mode.

It will be observed that the junction between the fixed resistor 109 and the thermistor 37 comprises a voltage take-off point for the triggering of the unijunction transistor 102 which is connected to operate as a monostable circuit, as will be discussed. When the switch 21 is in the position shown (i.e. the HOT mode), the thermistor 37 is on the lower voltage side of this take-off junction relative to the gate lead 101 so that as the temperature of the heat-transferring liquid increases, the resistance of the thermistor 37 will decrease correspondingly, and thereby reduce the take-off voltage from the voltage divider network comprising the resistor 109, thermistor 37, and one of the fixed resistors 111–115. This will retard the firing angle of triac Q1 and supply less current to the bank of thermoelectric diodes 76 until a state of equilibrium is reached.

When the switch 21 is switched to the COLD state (that is, the movable contacts are connected to the contacts 91, 94 and 97), the thermistor 37 is above the voltage take-off point of the voltage divider network. In this state, the voltage divider network includes the thermistor 37, the resistor 109, and one of the fixed resistors 117–121.

In summary, the voltage at the anode of diode 100 is a control signal representative of the difference between the actual temperature of the heat-transferring liquid (sensed by thermistor 37) and a desired temperature (as determined by the setting of the temperature control switches 110 or 116 depending upon the mode of operation).

A resistor 130 is connected between one power terminal of the unijunction transistor 102 and the lead 89, and a second resistor 131 is connected in the other terminal circuit of the unijunction transistor 102. The unijunction transistor 102 and its associated circuitry, particularly capacitor 103, resistors 105, 106 and the voltage divider circuitry feeding current to diode 100 is arranged so that the unijunction transistor 102 generates an output pulse for each cycle of the 60 Hz. input voltage. This output or trigger pulse is synchronous with the voltage being applied through transformer T1, bridge B1 and switch 75 to the bank of thermoelectric diodes 76. The triggering time within a given cycle will be advanced or retarded by the previously mentioned control signal depending upon the mode in which the switch 21 is set (hot or cold), the temperature of the liquid taken from the standpipe, and the particular setting of whichever of the temperature control switches 110, 116 is connected in circuit.

OPERATION

To summarize the operation of the control circuitry, assuming that the switch 21 is set in the "HOT" mode, as illustrated, a voltage divider network will be set up comprising resistor 109 in series with the thermistor 37 and one of the resistors 111–115, depending upon the setting of switch 110. The resistors 111–115 are calibrated such that a higher resistance value produces a higher operating temperature for the heat transferring liquid since it will advance the firing angle for the triac Q1.

The resistance of the thermistor 37 is an inverse function of temperature—that is, as temperature rises the ohmic resistance of the thermistor 37 decreases. Hence, for the "HOT" setting mentioned, as the temperature of the liquid flowing from the standpipe reservoir increases, the value of resistance of the thermistor 37 will decrease, thereby withdrawing some of the current that would otherwise be used to charge the capacitor 103 at the beginning of a cycle. Thus, the magnitude of the control signal will be reduced. This will retard the firing angle of the unijunction transistor 102. In other words, the charge on the capacitor 103 must build to a fixed point in order to trigger the unijunction transistor 102. The lower the value of resistance in the lower leg of the voltage divider network feeding the diode 100, the lesser current will be available to charge the capacitor 103, and this will retard the firing angle. Still referring to operation in the "HOT" mode, as the temperature of the liquid reduces, the value of resistance of the thermistor 37 will increase, and this will advance the firing angle for the unijunction transistor 102, as is desired because as the temperature of the heat-transferring liquid reduces while operating in the "HOT" mode, more electrical energy must be converted to heat energy by the thermoelectric diode bank 76 to reach an equilibrium.

When operating in the "COLD" mode, the position of the movable contacts of the switch 21 are reversed from those illustrated, thereby reversing the relative positions of the thermistor 37 and fixed resistor 110 in the voltage divider network feeding the diode 100. Again, the temperature is determined by the setting of the switch 116, and as the temperature of the liquid rises, the resistance value of the thermistor 37 will decrease. However because the resistor is now in the top leg of the voltage divider network, more current will be available to charge the capacitor 103, and this will advance the firing angle, as is desired when operating in the "COLD" mode and the temperature of the heat-transferring liquid rises. Conversely, when the temperature of the liquid reduces, the resistance value of thermistor 37 will increase, thereby reducing the current available to charge the capacitor 103 per cycle and retarding the firing angle, again achieving the desired result when operating in the "COLD" mode and the temperature of the liquid reduces.

Thus, the output signal of the unijunction transistor 102 is a voltage level or pulse which reduced to zero at the end of each cusp of the full-wave rectified input voltage. The firing angle is advanced or retarded as just discussed, and this signal is coupled to the gate lead of a Silicon Controlled Rectifier (SCR) 135. The output pulse of the SCR 135 is coupled through a diode 136 and a voltage divider network including resistors 140 and 141 to the gate lead G of the triac Q1, causing it to conduct, and thereby completing the circuit for the primary winding of transformer T1. When the circuit is completed, the sinusoidal input wave will energize bridge circuit B1 (and hence, the bank 76 of thermoelectric diodes) in the polarity selected by relay R1. Briefly, a triac is an AC switch such that when the input or control current reaches a certain value, the triac conducts causing a short circuit between the terminals MT1 and MT2. The triac is turned off when the polarity of the power reverses and the current fed to the gate lead falls below a predetermined value, such as five microamps.

Figure 4:
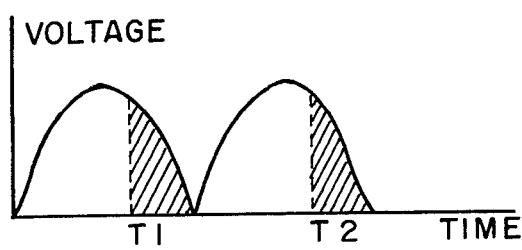
FIG. 4 is an idealized waveform of the voltage applied to the thermoelectric diodes, illustrating adjustment of the duty cycle.

In summarizing the operation of the control system, reference is made to FIG. 4 wherein two half-cycles of a full-wave rectified source voltage are shown. The polarity of this voltage as applied to the bank 76 of thermoelectric diodes is determined by the position of the contacts 75, which, in turn, is determined by the position of the deck 21A of the switch 21. Assuming that the system is operating in the "HOT" mode, and that the firing angle is the time T1 as indicated in the cycle, the shaded area indicates the amount of time during each cycle in which power is supplied to the bank 76 of thermoelectric diodes to generate heat. If the heat-transferring fluid becomes hotter, the resistance value of the thermistor 37 will decrease, and this will retard the firing angle to reduce the shaded area of FIG. 4 and to apply less average power to the diode bank 76. If, on the other hand, the temperature of the fluid reduces, the firing angle will be advanced and thereby provided more average power to the diode bank. When operating in the "COLD" mode, the operation of the circuitry is reversed because in this mode, as the temperature of the liquid rises, it is desired to increase the average power to the diode bank 76 (but in reverse polarity, of course) so as to withdraw more heat from the liquid.

The thermoelectric diode bank may have as many diodes connected in series branches with the branches connected in parallel, as are required for the amount of heating or cooling for which the system is designed. Thermoelectric diodes of this type are well known in the art, operating according to the Seebeck/Peltier effect, and they are commercially available.

To summarize the principal advantages of the invention, it avoids the use of a bulky, heavy compressor in providing cooling capability for medical applications. Not only is it lightweight and therefore portable, but the same source (namely, the thermoelectric diodes) is used both for heating and cooling the heat-transferring liquid which is transmitted to the applicator pad.

By using a minimal amount of heat-transferring liquid, (approximately two quarts or less in the total system), and by employing an applicator pad having a thin wall between the heat transfer liquid and the applicator surface, very rapid response times can be achieved for reducing the temperature of the surface to which the applicator pad is applied. This is particularly useful in skin grafts or the like, where it is also useful to achieve a very rapid and substantial temperature change, such as going from extreme "HOT" to very "COLD" or vice versa. By placing the temperature-sensitive thermistor adjacent the outlet of the liquid reservoir and by controlling the temperature of the liquid after it is removed from the reservoir, very close tolerances can be held on the temperature of the liquid, and response time is further reduced. This also facilitates producing large temperature changes with a minimum of heat-pumping capacity.

The use of a peristaltic pump provides excellent electrical isolation between the fluid loop and the applicator surface, and the use of the pressure relief valve in the manifold minimizes accidental spilling of liquid should the flexible applicator pad or tubing leading thereto become occluded.

By using a second peristaltic pump and independent fluid system, one of the fluid loops can be sterile, for use in flushing an organ with saline, and the temperature of the second loop may be independently variable.

The heat exchanger may take the form of a rectilinear copper fluid exchanger having a ½ inch conduit milled for conducting the fluid. A first set of four thermoelectric diodes are silver-soldered to the outer surface of one side of the exchanger, and these are connected in series electrically. A second set of four thermoelectric diodes are silver-soldered to the outer surface of the opposite side of the exchanger, and these are also connected in series electrically. The first set of diodes is connected in parallel with the second set.

Having thus described in detail a preferred embodiment of the present invention, persons skilled in the art will be able to modify certain of the structure which has been disclosed and to substitute equivalent elements for those illustrated while continuing to practice the principle of the invention; and it is, therefore, intended that all such modifications and substitutions be covered as they are embraced within the spirit and scope of the appended claims.

I claim:

1. Apparatus for selectively heating or cooling a local area of the body comprising: a source of heat transferring liquid; an applicator pad adapted to be applied to said local area and including means defining a conduit for carrying said liquid through said pad; heat exchanger means receiving said liquid and including thermoelectric diode means for producing heat when an electrical potential of one polarity is applied thereto and for absorbing heat when an electrical potential of the opposite polarity is applied thereto; pump means for pumping said liquid from said source through said heat exchanger means and said applicator pad; and control circuit means including temperature-sensitive means responsive to the temperature of said liquid for controlling the polarity and duration of application of an electrical potential to said thermoelectric diode means under operator control.

2. The apparatus of claim 1 wherein said temperature-sensitive means of said control circuit means comprises thermistor means arranged to sense the temperature of said liquid just prior to its entry into said heat exchanger means, said control circuit means further including adjustable resistive circuit means connected in circuit with said thermistor means and settable by an operator for generating a control signal representative of a difference between a desired operating temperature and the actual temperature of said liquid; and semiconductor switch means responsive to said control signal for controlling the application of electrical energy to said thermoelectric diode means for bringing the temperature of said liquid to the desired operating temperature for said system.

3. The system of claim 2 further comprising a manifold including a first conduit for communicating liquid from said source to said heat exchanger means, said thermistor being located in said first conduit; a second conduit for communicating said liquid from said heat exchanger to said pump means; a third conduit for communicating liquid from said pump means to said applicator pad; and a fourth conduit for communicating liquid from said applicator pad to said source of liquid.

4. The apparatus of claim 3 further comprising a pair of flexible conduits communicating said liquid between said manifold and said pad; pressure relief valve means in said manifold responsive to the liquid pressure in said third conduit for opening a valve to admit liquid from said third conduit to said fourth conduit to return the same to said source of liquid when an occlusion occurs in said applicator pad or said conduits. communicating said manifold with said pad.

5. The apparatus of claim 1 wherein said pump means includes a peristaltic pump, said system further comprising continuous conduit means connecting the input of said pump with the outlet of said heat exchanger means, and the outlet of said pump with said applicator pad.

6. Control apparatus is a system for selectively heating or cooling a local area of the body by means of an applicator pad having fluid continuously pumped through it, comprising: heat exchanger means including a plurality of thermoelectric diode means for producing heat when an electrical potential of one polarity is applied thereto and for absorbing heat when an electrical potential of the opposite polarity is applied thereto; thermistor means sensing the temperature of liquid flowing into said heat exchanger means; control circuit means including settable resistive means in circuit with said thermistor for generating a signal representative of the difference between the temperature of said liquid and a desired temperature for said liquid; circuit means responsive to said control signal for selectively applying voltage of a desired polarity to said thermoelectric diode means to bring the temperature of said liquid to said desired temperature.

7. The apparatus of claim 6 further comprising a source of alternating voltage; double-pole double-throw switch means operable by an operator for selectively coupling said source of voltage to said thermoelectric diodes; and semiconductor switch means in circuit with said source of voltage for establishing continuity of said source in response to said control signal.

8. The system of claim 7 wherein said circuit means comprises a monostable circuit responsive to said control signal and energized in synchronism with said alternating source of voltage for said thermoelectric diodes and controlling the switching of said alternating source to energize said thermoelectric diode means.

9. The apparatus of claim 8 further comprising manually-settable switch means for actuating said apparatus in a HOT mode or a COLD mode, said monostable circuit means being actuable to advance the triggering angle of said semi-conductor switch means in the HOT mode when said thermistor indicates the temperature in said fluid reduces, and to retard the firing angle of said semiconductor switch means when said thermistor indicates that the temperature of said liquid increases.

10. The apparatus of claim 9 wherein said monostable circuit means in said COLD mode advances the firing angle of said semiconductor switch means when the temperature of said liquid rises, and retards the firing angle of said semiconductor switch means when the temperature of said liquid reduces.

11. The apparatus of claim 6 further comprising first and second visual indicators responsive to said manually-controlled switch means for indicating whether said system is set to operate in a HOT mode or a COLD mode.

12. Apparatus for selectively heating or cooling a local area with a fluid-filled applicator pad and for independently selectively heating or cooling a second liquid comprising: first and second independent sources of heat transferring liquid; means for communicating said first source of heat-transferring liquid with said applicator pad; first and second heat exchanger means; a first peristaltic pump for pumping said first liquid through said heat exchanger means and said applicator pad; a second peristaltic pump for pumping said second liquid from said second source through said second heat exchanger to an outlet conduit for application; and first and second independent control means, each associated with a respective one of said first and second liquids for selectively controlling the temperature thereof in response to a manual setting.

13. The apparatus of claim 12 further comprising means for connecting said first and second peristaltic pumps in tandem; and motor means for driving said pumps in tandem.

* * * * *